United States Patent [19]

Reese

[11] 4,200,625

[45] Apr. 29, 1980

[54] IMMOBILIZED BINDER FOR AUTOMATED ASSAY

[75] Inventor: Max G. Reese, Salt Lake City, Utah

[73] Assignee: Becton, Dickinson and Company, Paramus, N.J.

[21] Appl. No.: 923,711

[22] Filed: Jul. 12, 1978

[51] Int. Cl.$^2$ .................... G01N 33/16; A61K 43/00; B01J 1/22; G21H 5/02

[52] U.S. Cl. .................................... 424/1; 23/230 B; 424/12

[58] Field of Search .................... 424/1, 12; 23/230 B, 23/253

[56] References Cited

U.S. PATENT DOCUMENTS

| | | |
|---|---|---|
| 3,896,217 | 7/1975 | Johnson .................................... 424/1 |
| 4,039,652 | 8/1977 | Adams et al. ............................. 424/1 |
| 4,125,375 | 11/1978 | Hunter ................................. 23/230 B |
| 4,128,628 | 12/1978 | Brooker et al. ..................... 23/230 B |

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

In an automated assay employing a reusable immobilized binder in a flow-through chamber, the binder is supported on a cotton support preferably mercerized absorbent cotton. Such cotton support prevents plugging when using free serum or plasma samples, and in addition, does not compress, has good flow properties, is easily handled, has low non-specific binding of proteins and steroids and is stable.

11 Claims, No Drawings

IMMOBILIZED BINDER FOR AUTOMATED ASSAY

This invention relates to an array and more particularly to a new and improved immobilized binder for an automated assay employing a reusable binder.

U.S. Pat. No. 3,896,217 discloses an assay in which a binder covalently bound to a substrate is regenerated by flowing an eluting solution therethrough. By this system, the binder may be repeatedly reused.

An automated assay is described in U.S. Pat. No. 4,009,005 which sets forth in more detail the various aspects of equipment for the assay employing a reusable binder.

The systems of the above patents relate principally to a flow-through type of system, and in employing such a flow-through system, if there is a plug up of flow passages, the use and reuse of the binder is adversely affected. Such adverse affects are shown by physical plugging which prevents flow and thus interference with subsequent tests or by a decrease in the flow rate through the immobilized binder which decreases the speed of the assay.

In an automated assay employing a reusable binder, such plugging is a problem, as compared to prior art systems which employ a single use binder in that the use of such single use binders flow through and repeated flow-through of sample is not of major consequence.

One source of plugging are the proteins, other than the ligand to be analyzed, which may be present in the sample. If undiluted serum is assayed in such a system, the relatively large proteins tend to plug up the immobilized binder. The serum may be diluted to reduce the concentration of proteins for better flow through the immobilized binder; however, such dilution reduces the concentration of the ligand to be assayed in the serum. Where the concentration of ligand is relatively low; e.g., digoxin or $T_3$, diluting the serum reduces the concentration even more and presents problems in accurately and reliably assaying for the relatively small amounts of ligand present in the diluted serum. Thus, dilution to avoid a plugging problem leads to problems of accurate assay; i.e., the sensitivity is less than desired.

In accordance with the present invention there is provided an improvement in an assay wherein a ligand to be assayed and a labeled form of the ligand are caused to flow through a chamber having a binder specific for the ligand supported on a solid substrate and wherein the binder is regenerated for reuse in the assay by releasing ligand and labeled ligand from the binder, with such improvement being the use of absorbent cotton, as the solid substrate on which the binder is supported. Applicant has found that such cotton substrate does not lead to plugging when serum or plasma samples are passed therethrough. In addition, such cotton substrate does not compress, has good flow properties, is easily handled, can be easily derivitized for covalent linking of binder thereto, has low non-specific binding of proteins and steroids and is stable.

The cotton employed as the support is fibrous cotton which can be woven or non-woven, with the cotton preferably being non-woven or loosely woven in that it permits the use of a greater amount of material in a given volume. The cotton is most preferably an absorbent cotton and in particular mercerized absorbent cotton in that such cotton has increased binding capacity.

A binder may be conveniently supported on the cotton substrate employed in the present invention by effecting activation thereof with cyanogen bromide by procedures generally known in the art, followed by covalent linking of the binder to the cotton. In brief, such a procedure involves contacting the cotton substrate with cyanogen bromide at a basic pH, generally in the order of from 10.0 to 12.0, followed by washing and air drying. The thus activated cotton substrate may then be covalently bonded to the binder to be used in the assay, by procedures known in the art. A general procedure for effecting activation with cyanogen bromide and subsequent covalent linking to a binder is described in U.S. Pat. No. 4,059,685, with respect to dextran, and such a procedure may also be employed for covalently linking a binder to the cotton substrate employed in the present invention.

Although activation by the use of cyanogen bromide is preferred, other procedures for covalently linking a binder to the cotton substrate may be employed within the spirit and scope of the present invention. Thus, for example, as described in U.S. Application Ser. No. 774,390, filed on Mar. 4, 1977, the cotton substrate may be treated with a halogenated acid such as bromoacetic acid to form a carboxyl derivative, which may then be treated with thionyl chloride to form the acid chloride which is then further treated with sodium azide to form an acylazide derivative to which a binder can be conjugated.

The cotton substrate having a binder covalently linked thereto is employed in an assay by placing such substrate in a chamber of the type described in U.S. Pat. No. 4,059,685 which is employed in an automated assay of the type described in U.S. Pat. No. 4,009,005, both of which are hereby incorporated by reference. In accordance with such assay, the ligand to be assayed and a form of such ligand are caused to flow through the chamber having a binder specific for the ligand covalently attached to the cotton substrate, and a portion of both the labeled and unlabeled ligand become bound to such binder in the chamber, and another portion of such labeled and unlabeled ligand passes through the chamber to a detector where it is quantitated. Subsequently, an eluting solution is flowed through the chamber to free both the labeled and unlabeled ligand bound to the binder covalently linked to the cotton substrate. The labeled and unlabeled ligand freed from such binder by the eluting solution flows to a detector where it is quantitated. Following elution to free the ligand, the binder covalently linked to the cotton substrate is rinsed and ready for reuse in the next and subsequent cycles. In accordance with the present invention, it has been found that samples can be caused to pass through such chamber without plugging thereof, and without the necessity of effecting high dilution of such samples whereby there is not a significant reduction in the concentration of the ligand to be assayed, thereby increasing the apparent sensitivity of the assay. Thus, for example, it has been found that samples of high serum content; e.g., up to 100 percent, can be employed without plugging.

The present invention is applicable to assays for a wide variety of ligands for which an appropriate binder can be found, such as (1) antigens, which when introduced into the blood stream of a vertebrate result in the formation of antibodies; (2) haptens, which when bound to an antigenic carrier and introduced into the blood stream of a vertebrate produce antibodies specific for the hapten (haptens are sometimes interchangeably referred to as antigens); or (3) ligands which have naturally occurring binders which can be isolated in a form specific for the ligand, such as, for example, serum proteins (thyroxine binding globulin, which is a binder for thyroxine, and triiodothyronine) binders extracted from various animal organs, serums, milk binders and the like. It is also to be understood that in some cases, the ligand to be assayed is an antibody, in which the binder would be an antigen.

As representative examples of ligands which can be assayed in accordance with the present invention, there may be mentioned: polypeptides, nucleotides, nucleosides and proteins, such as ACTH, oxytocin. lutenizing hormone, insulin, proinsulin, Bence-Jones protein, chorionic gonadotropin, pituitary gonadotropin, growth hormone, renin, thyroxine binding globulin, bradykinin, angiotensin, follicle stimulating hormone; cyclic AMP; cholyglycine, cyclic GMP, etc.; steroids, including: estrogens, gestrogens, androgens, andrenocortical hormones, bile acids, cardiotonic glycosides, aglycones as well as saponins. As specific examples of ligands there may be mentioned: thyroxine, triiodothyronine, testosterone, androsterone, equilenin, estrone, estriol, progesterone, pregnenolone, 17-hydroxydioxycorticosterone (compound S), deoxycorticoserone, cortisone, corticosterone, cortisol, aldosterone, digoxin, digitoxin, etc.; vitamins, such as folic acid, the B vitamin group, the D vitamins and miscellaneous ligands, such as antigens for Viral Hepatitis A and B, Rubella, Herpes Simplex, α-fetoprotein, etc.

The labeled ligand employed in the assay can be the ligand or an appropriate analog thereof, provided that the ligand to be assayed and labeled ligand are both specifically bound by the binder employed in the assay. The "label" or "tab" may be any one of a wide variety of "labels" or "tags", including radioisotopes, enzymes, fluoroescent materials, etc. with a radioisotope, such as a radioisotope of iodine, tritium, cobalt and the like, being preferred.

The present invention will be further described with respect to the following example; however, the scope of the invention is not to be limited thereby.

EXAMPLE

I. Mercerization of Cotton

1. Imerse cotton in 4N NaOH, flush container with nitrogen, seal and store 24 hours at 4° C.
2. Wash thoroughly the next day with distilled water until the washes are neutral pH. Wash twice in phosphate buffer pH 7.5 and once again with distilled water. Pat dry and store in an air tight container.

II. Activation of Cotton

1. Dissolve 20 grams CNBr/200 ml distilled water.
2. In a separate vessel place the cotton (approximately 1.5 g) in 400 ml phosphate buffer 0.5 M pH 11.0 and stir. Maintain the temperature at 4°–10° C.
3. Add the 20 grams dissolved CNBr to the stirring cotton slowly. Total time of reaction approximately 10 minutes.
4. Wash the cotton with pre-chilled distilled water.
5. Wash the cotton with increasing concentrations of acetone in water to 100% acetone. The cotton is now ready to store dry or use immediately for conjugating of antisera.

III. Conjugation

1. One ml of antisera with one ml of 0.1 M sodium bicarbonate is dialyzed against distilled water at room temperature for 1 hour and then overnight at 4° C. against 0.1 M sodium bicarbonate.
2. Approximately 200 mg of activated cotton is used to conjugate 50 μl of the above dialyzed antisera diluted in 1.5 ml of 0.1 M sodium bicarbonate at pH 9.5. The conjugation vessel is sealed and rotated at 4° C. for three days.
3. The conjugate is then washed in distilled water and phosphate buffer 0.05 M pH 7.5. Store in the phosphate buffer 0.05 M pH 7.5 at 4° C.

IV. Chamber Preparation

1. A teflon chamber with an inside diameter of 0.149 inches is filled with the conjugate (approximately 50 mg).
2. The end pieces are pressed into place and the chamber is ready for use.

V. Digoxin Assay Protocol

A. Reagents & Materials
(1) Digoxin antibody chamber: containing antibody covalently attached to cotton.
(2) Digoxin standards: containing digoxin in stabilized 100% human serum.
  0
  0.5 ng/ml
  1.0 ng/ml
  2.0 ng/ml
  4.0 ng/ml
  8.0 ng/ml
(3) Adsorption buffer: phosphate buffer 0.05 M, pH 7.5, and 0.15 M sodium chloride.
(4) Elution buffer: phosphate buffer 0.05 M, pH 8.25 diluted with equal volumes of methanol.
(5) $^{125}I$ digoxin tracer.

The assay is effected in automated apparatus as described in U.S. Pat. No. 4,009,005, with such apparatus being available from Becton, Dickinson Immunodiagnostics, Automated Immunochemistry Systems. Such equipment is identified by the mark ARIA II.

The present invention is particularly advantageous in that an assay including regeneration and reuse of a binder can be effected without plugging of the chamber including immobilized binder, and without the necessity of effecting high dilution of the serum samples and/or taking preliminary steps to avoid such plugging. In addition, by employing a cotton substrate in accordance with the present invention, such plugging problems are eliminated, while retaining the advantages of the supports previously employed in such assays; i.e., good flow properties, low non-specific binding of proteins and steroids, and the like.

In addition, the use of such a substrate increases the apparent sensitivity of the assay by eliminating the necessity for high dilution of serum of plasma samples.

Numerous modifications and variations of the present invention are possible in light of the above teachings and, therefore, within the scope of the appended claims the invention may be practised otherwise than as particularly described.

I claim:
1. In an assay wherein a ligand to be assayed and labeled form of the ligand are caused to flow through a chamber having a binder specific for the ligand sup- ported on a solid substrate, and wherein the binder is regenerated for reuse in the assay by releasing ligand and labeled ligand from the binder, the improvement comprising:

employing fibrous cotton as said solid substrate.

2. The assay of claim 1 wherein the cotton is an absorbent cotton.

3. The assay of claim 2 wherein the absorbent cotton is mercerized absorbent cotton.

4. The assay of claim 3 wherein the binder is covalently linked to the cotton support.

5. The assay of claim 4 wherein the labeled ligand is radiolabeled.

6. The assay of claim 5 wherein the binder is an antibody.

7. The assay of claim 5 wherein the ligand to be assayed is in a serum sample.

8. In a flow-through chamber for an assay for a ligand including a binder specific for the ligand supported on a solid substrate wherein the ligand to be assayed and labeled form of the ligand are caused to flow through the chamber and wherein the binder is regenerated for reuse in the assay by releasing ligand and the labeled form of the ligand from the binder, the improvement comprising:

employing fibrous cotton as said solid substrate.

9. The flow-through chamber of claim 8 wherein the cotton is an absorbent cotton.

10. The flow-through chamber of claim 9 wherein the absorbent cotton is mercerized absorbent cotton.

11. The flow-through chamber of claim 10 wherein the binder is an antibody.

* * * * *